United States Patent [19]

Meister et al.

[11] Patent Number: 5,125,032

[45] Date of Patent: Jun. 23, 1992

[54] TALK/LISTEN HEADSET

[76] Inventors: Erwin Meister, Oberbreiti 96, 8454 Buchberg; Edwin Bollier, Im Straler 40, 8047 Zurich, both of Switzerland

[21] Appl. No.: 442,146

[22] Filed: Nov. 28, 1989

[30] Foreign Application Priority Data

Dec. 2, 1988 [CH] Switzerland .................. 04476/88

[51] Int. Cl.$^5$ .................. A61F 11/06; H04R 1/10; H04R 25/00
[52] U.S. Cl. .................. 381/183; 381/72; 381/74; 381/151
[58] Field of Search .................. 381/72, 151, 74, 114, 381/173, 183; 379/430; 455/89, 90

[56] References Cited

U.S. PATENT DOCUMENTS

| | | | |
|---|---|---|---|
| 3,869,584 | 3/1975 | Wilde | 381/183 |
| 4,025,734 | 5/1977 | Aloupsis | 381/74 |
| 4,087,653 | 5/1978 | Frieder, Jr. et al. | 379/430 |
| 4,516,428 | 5/1985 | Konomi | 381/151 |
| 4,535,205 | 8/1985 | Ravinet et al. | 381/173 |
| 4,591,668 | 5/1986 | Iwata | 381/151 |
| 4,677,678 | 6/1987 | McCutchen | 381/72 |
| 4,833,719 | 5/1989 | Carme et al. | 381/72 |

FOREIGN PATENT DOCUMENTS

| | | | |
|---|---|---|---|
| 0153490 | 9/1983 | Japan | 381/151 |
| 0208998 | 11/1984 | Japan | 381/74 |
| 2198612 | 6/1988 | United Kingdom | 379/430 |

Primary Examiner—James L. Dwyer
Assistant Examiner—Jason Chan
Attorney, Agent, or Firm—Burns, Doane, Swecker & Mathis

[57] ABSTRACT

In a talk/listen headset, essentially comprising two ear protection capsules (1, 2) connected to one another via a headband (3), two microphones (6, 7) are located in one of these along a vertical (9) which runs, projected on the head of the wearer, through the middle of the temporal bone and extends up to the mandibular angle. While the upper microphone (6) acts in the area of the end of the zygomatic arch, the lower microphone (7) is located in the area of the articular process of the ascending ramus of the jaw. Both microphones (6, 7) react to solid-borne sound and are piezoelectric resonators with a mass-forming body, an impedance converter and a filter/equalizer, the microphones being connected to one another in terms of voltage in order to absorb or compensate the local tone amplitudes to the bottom and to the top caused by the reproduction. This has the effect that this indirect reproduction of the voice is optimised in terms of tone and timbre. The ear protection capsules (1, 2) also contain earphones (4a, 4b) and one receiving element (12a, 12b) each. The latter are directed towards the background noises. Microphones (6, 7), earphones (4a, 4b) and receiving elements (12a, 12b) interact with an electronic component (13) integrated in the ear protection capsules, the circuit of which component has, inter alia a communication priority in favor of the microphones and earphones and not in favor of the receiving elements.

8 Claims, 6 Drawing Sheets

TALK/LISTEN HEADSET

The present invention relates to a talk/listen headset, comprising earpiece bodies in which at least one earphone and at least one microphone reacting to solid-borne sound are integrated.

BACKGROUND OF THE INVENTION

Sometimes communicating by voice in areas subject to noise influences is not only problematical, but is even often impossible. To begin with, the speaker might be able to be heard by raising his voice, but after a short while, due to the vocal chords tiring, he will regularly switch over to communication by means of gesticulation, with all the disadvantages associated therewith, both at the speaker who can no longer communicate everything and at the hearer who will seldom understand much of it. Difficulty in communication may, depending on the location, have catastrophic results, either because economic damage can result or because, which would then be far worse, people could be endangered as a result. In addition, there are activities in our society where perfect communication under difficult conditions constitutes a mandatory requirement: these include, for example, communication between pilots and ground control, communication in and out of engine rooms, emergency operations in a noisy environment etc.

PRIOR ART

Talk/listen headsets are commercially available which comprise a headphone and a microphone placed at mouth level (lip microphone). Reception is here not a problem as such, provided that the headphone capsules have an ear protection design, and the earphone units are placed therein. The optimum noise insulation by virtue of an ear protection design of the headset cuts the wearer off from external emissions very well. The quality of reception of communications is maximised by virtue of such measures. In contrast, the talking function is far more complex: disadvantages regularly have to be taken into account relating to the design of this aid, with respect to the outlay necessary for providing a microphone of sufficient quality. According to the known latest prior art, the talking function is performed by a dynamic, noise-compensating lip microphone with which the background noises are to a large extent suppressed, always provided that this microphone is handled according to the operating instructions within narrow tolerances. It is obvious that a projection of this type in the area of the lips can occasionally prove to be an extreme nuisance. Moreover, if a rest position is assumed, the readiness to talk must be established anew each time again, which often leads to enervating attempts, in that it is necessary to send a whole range of communication messages back and forth between sender and receiver. Starting from a rest position, therefore, the readiness to talk can always be established with a time delay and additional effort. This lack of immediacy can have far-reaching negative consequences.

Talk/listen headsets have become known in which speech is transmitted with a throat microphone. These microphones are really only a substitute for lip microphones which are exposed to too great a background noise and hence can no longer provide satisfactory quality for transmission. As regards the use of throat microphones, it should be taken into consideration that these have a basic disadvantage arising from the voice pick-up point. Throat microphones transmit the voiced sounds-produced in the larynx and cannot reproduce the individual timbre produced by the mouth cavity, tongue, lips etc. Moreover, throat microphones also need to be repositioned every time out of the rest position for renewed readiness to talk.

German Patent 2,230,637 describes a talk/listen headset which rests in the area of one ear and leaves the other free, comprising a casing in which there is an earphone and a microphone reacting to solid-borne sound. The casing is here formed as a toroidal ring which lies around one ear, but leaves it free. This is aimed at permitting a binaural hearing of the background noises. A funnel-shaped sound line leads the sound power output by the earphone to the ear input located approximately in the middle of the casing. The microphone reacting to solid-borne sound, which is preferably a moving-coil pressure gradient microphone, is exited in the region of the temporo-mandibular joint. The disadvantages of this proposal are constituted by the fact that, in order to permit binaural hearing of the background noises, the organs of hearing are left unprotected from high volume levels, as a result of which the field of application of a headset of this kind remains very limited. Moreover, even if an inherently bulky moving-coil pressure gradient microphone is used, the degree of efficiency with respect to the tonality and characteristics of the reproduced voice remains low, as a result of which additional aids are necessary if a satisfactory reproduction is to be provided. This could be rectified to a large extent by installing an amplifier, although undesired ambient noise would again likewise then be amplified, which does not promote the general comprehensibility. Finally, it should also be pointed out that the background noises collide negatively with radio-based or wire-based listening.

OBJECT OF THE INVENTION

The invention is intended to provide assistance here. The object of the invention, as is characterized in the claims, is- to improve a talk/listen headset of the type mentioned at the beginning to such an extent that first of all an ear protection function is ensured. It is also the object of the invention to substantially improve and simplify the reproduction quality of the microphone reacting to solid-borne sound. Furthermore, it is the object of the invention to permit a stereophonic reception of the background noises, despite the ear protection function of the headset, with definition of a communication priority over the microphones and earphones, in order to prevent a collision between the two functions.

ADVANTAGES OF THE INVENTION

The advantages of the invention are essentially to be seen in the fact that the talk/listen headset that is primarily designed for ear protection does not cut off the wearer completely from the background noises: each ear protection capsule is equipped with a receiving element directed outwards which is designed to receive the background noises. However, in order that the cutting-off effect of the ear protection capsules is not thereby lost, the receiving elements interact with an electronic component, the circuitry of which has means for regulating the incoming sound from the surroundings to a volume level that is normal for the ear. The organs of hearing are protected optimally by means of this measure, moreover the stereophonic reception of the background noises via the receiving elements makes it possible for the wearer of the talklisten headset to decide the direction the sound is coming from, as is always the case with normal hearing. The design according to the invention of the microphone reacting to solidborne sound also proves to be advantageous: by using a piezoelectric resonator which interacts with a massforming body, which acts on the oscillation amplitudes from the resonator, a sharper resonance is achieved, which permits an improvement in the quality of reproduction. Additionally accommodated in the compact unit of this microphone according to the invention are also an impedance converter and a filter/equaliser, which likewise interact with the remaining elements of the microphone and help to improve the qualitative degree efficiency further in the transmission of the voiced sounds of greater speech comprehensibility: the impedance converter matches the impedance to a downstream radio device; finally the filtering (filter/equaliser) has an effect on the presence of speech, as a result of which the speech comprehensibility is decisively improved. Great advantages are then also evident each time the talk/listen headset according to the invention is donned, for the latter makes do without additional head fastenings, in contrast to the known headsets. As regards the accommodation of the microphones in the ear protection capsules, the proposed method also proves advantageous in an additional manner: the microphone integrated in a noise-protected ear protection capsule is protected from the background noise as is the earphone likewise accommodated there, in that the former is also placed in a capsule niche. If two microphones are provided, it is possible to mix the individual solidborne sound frequencies depending on the respective pickup point with one another in such a way that a frequency spectrum with a broad comprehensibility results therefrom. In this connection, it can be established that, along a vertical band width of about 1 cm which runs, in the case of ear protection capsules on a person, approximately centrally through the temporal bone (os temporale) and extends up to the mandibular angle (angulus mandibulae), different indirect body voice frequencies arise which, combined in terms of voltage, produce a middle term quality of the voice as a result: thus, higher tones are produced in the area of the end of the zygomatic bone (arcus zygomaticus), whereas further down, in the area of the ascending ramus of the jaw (processus condylaris mandibulae) lower tones can be found. A further advantage of the invention is to be seen in the fact that, by eliminating acoustic feed-backs, a duplex-capable (telephone effect) talk/listen headset can be provided. The basis of this effect can be seen in the fact that there is a separation in terms of sound between earphones and microphones, in that the microphones themselves are cut off with respect to noise and have a spring suspension. A further advantage of the invention is to be seen in the fact that measures have been taken so that the wireless or wire-based communication via the earphones and microphones does not collide with the perceivable background noises via the receiving elements. If the earphones and/or the microphones are being used for communication, a communication priority of these elements always prevails over the receiving elements for registering the background noises: sound emissions from the surroundings are not forwarded by the receiving elements to the earphones, since their activation remains completely disconnected during this phase. After communication has ended, reception of the background noises via the receiving elements begins functioning again after a given delay, that is the wearer of the talk/listen headset again has contact with his "outside sound world" to a certain degree despite the ear protection isolation.

Advantageous and expedient further developments of the problem solution according to the invention are characterized in the further dependent claims. Attention is drawn in particular here to the voice-controlled switching for creating the communication priority, or the voice-controlled sending/receiving switch-over of the radio device. Furthermore, the advantageous design of the talk/listen headset for people with hearing defects are also to be emphasised.

Exemplary embodiments of the invention are described in greater detail below with reference to the drawing. All elements not necessary for immediate comprehension of the invention have been omitted. Identical elements are denoted by the same reference numerals in the various figures.

DESCRIPTION OF THE EXEMPLARY EMBODIMENTS

Figure 1:
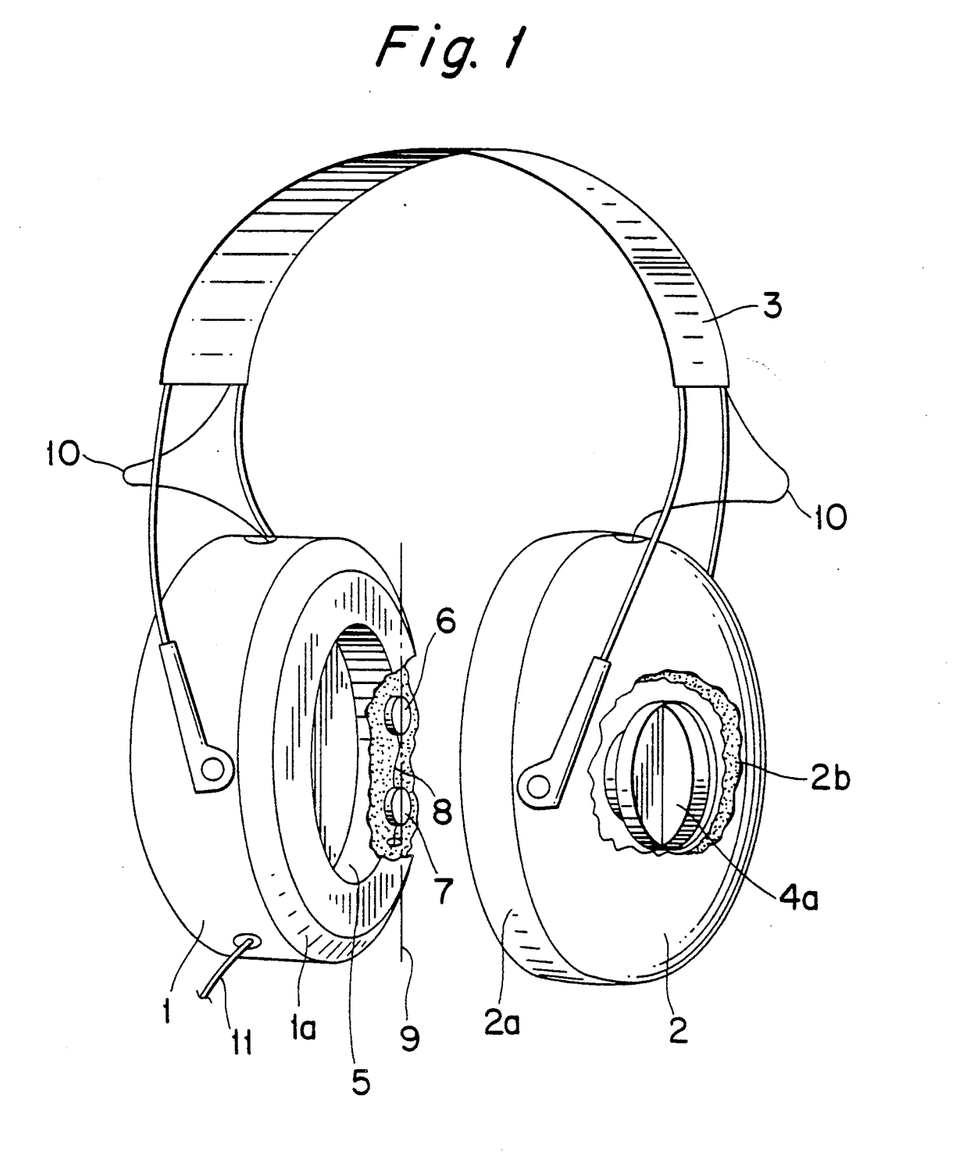
FIG. 1 shows a talk/listen headset which is designed as ear protection headset.
Figure 3:
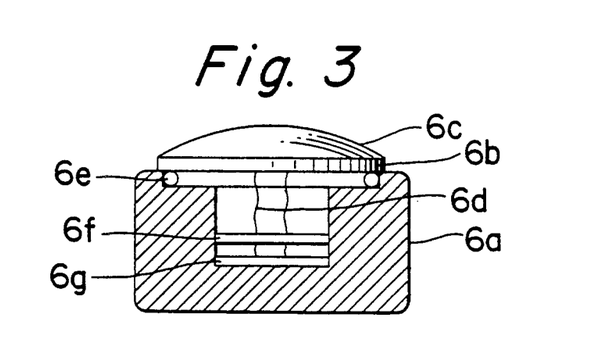
FIG. 3 shows a microphone reacting to solid-borne sound.
Figure 7:
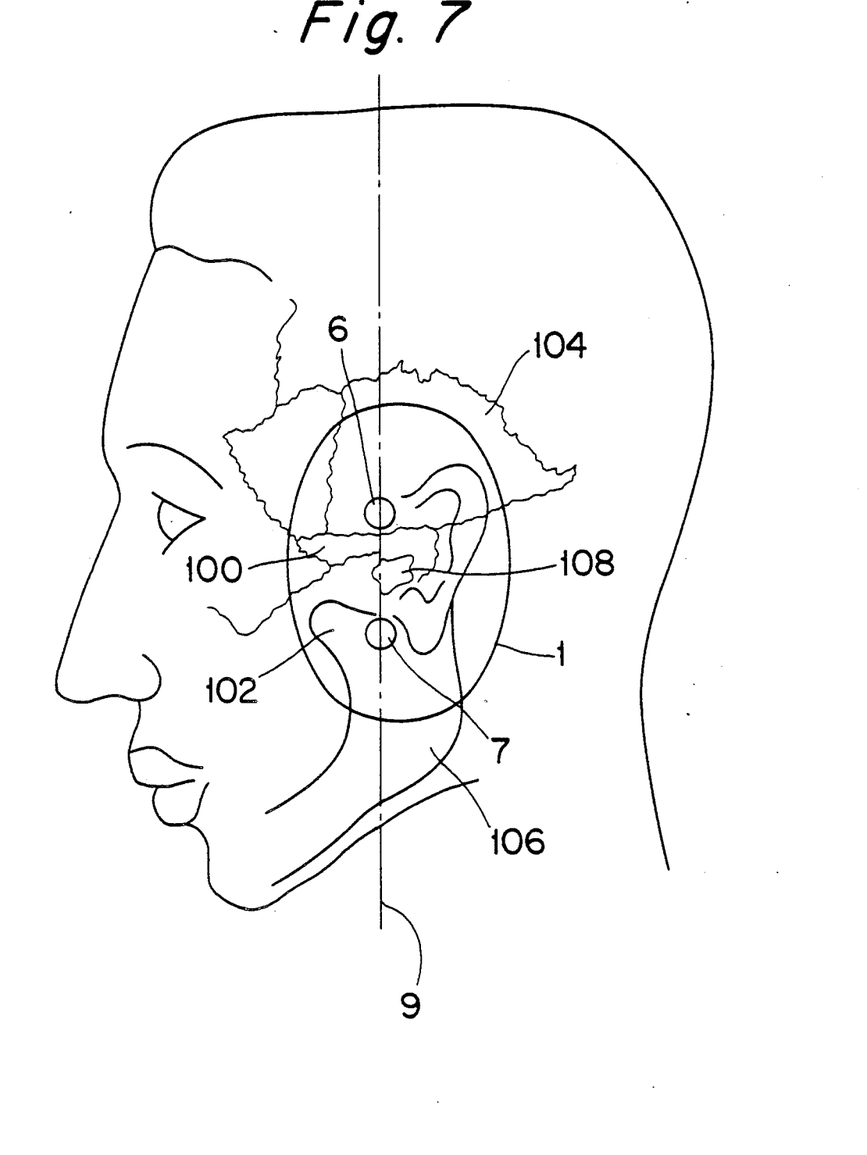
FIG. 7 is a diagram of the location of the talk/listen headset on a user's head.

FIG. 1 shows a talk/listen headset which performs the functions of ear protection, sending and receiving. It consists of two ear protection capsules 1, 2, connected to one another by a head band 3, which are designed for ear protection, as is indicated by the cushion 1a, 2a and the insulation 2b of the only ear protection capsule 2 cut open. To increase the comfort when wearing such a talk/listen headset, a soft padding is to be provided on the parts lying against the ears, there being no pressure exerted on the ear itself as a result of appropriately designed earpiece openings 5. Pressure compensation openings (not visible) integrated in the ear protection capsules 1, 2 prevent any excess pressures on the ear drum of the wearer. In the ear protection capsule 2, an earphone 4a can be seen which is cut off optimally from background noise by the insulation 2b surrounding it. Regularly provided and advantageous is if the other ear protection capsule 1 is also equipped with an earphone if it is not intended to provide monaural hearing function. It can be seen that the present talk/listen headset is equipped with two earphones from the way line 10 is laid, which connects the two earphones in terms of current (see so the diagram in FIG. 4). The ear protection capsule 1, which is provided for the left ear, which at the same time indicates that the talk/listen headset is represented in the drawing in the direction it is worn, has two microphones, 6, 7 which are placed below the covering of cushion 1a. The niches in the cushion 1a provided for the microphones 6, 7 should be designed so that the microphones 6, 7, which preferably have the shape of a dome and a mean diameter of approx. 5-15 mm and a thickness of a few millimetres, can be anchored well therein, but at the same time can also develop a certain resilience to impact. Also, the anchoring of the microphones 6, 7 should be designed so that the greatly vibrating contact diaphragm of these microphones is always in the area of reception, that is in the case of talk/listen headsets on a person, the contact diaphragms should press directly against the covering of the cushion 1a. The material of the covering is neutral with regard to damping, in order not to indicate an impairment of these microphones reacting to solid-borne sound. FIG. 7 shows a typical position of the microphones 6, 7 with pick-up of the solid-borne sounds at two places. The microphones 6, 7, the design of which is described in detail under FIG. 3, are placed so that when the talk/listen headset is worn the upper microphone 6 picks up the solid-borne sounds in the area of the end of the zygomatic arch 100 (arcus zygomaticus); the lower microphone 7 is placed on the other hand in the area of the articular process 102 of the ascending ramus of the jaw (processus condylaris mandibulae). If the two microphones 6, 7 are connected by an imaginary vertical 9, then an extension of the same upwards goes through the temporal bone 104 (os temporale) approximately in the middle; an extension of this vertical 9 downwards exits the head in the area of the mandibular angle 106 (angulus mandibulae). Within the area of a band width of approx. 1 cm of this imaginary vertical 9, the reception of the solid-borne sounds from the speech sounds can be classified as good, provided that efficient microphones are provided. As regards the formation of the speech sounds, the following should be noted: voiced sounds are produced in the larynx which build on the fundamental tone. This primary larynx tone is then transformed in the area of the voice-forming part of the larynx (glottis) such that a certain, but still rudimentary voice is produced therefrom by resonatory transformation. This voice received its final modelling as a consequence of the individual characteristics of other speech-forming organs, such as tongue, lips, lower jaw structure, vellum, teeth etc. of the speaker. If one considers the sounds from the larynx, it can be established that the average proportion of the high frequency tones produced there is only 20% of the whole spectrum; the proportion of the low frequency (LF) tones is thus in contrast approximately 80%. It must also be taken into consideration that the physiological components of the noise portions in the larynx are relatively high even at a normal speech volume. Accordingly, when the sounds are normally picked up from the larynx a satisfactory reproduction of the speech cannot be expected, for the simple reason that a timbre is not yet present there, or has not yet taken shape enough. Although in the case of the reproduction of speech sounds using the microphones 6, 7 shown in FIGS. 1 and 2, this is an indirect transmission, nevertheless a comparatively excellent quality can be expected, in conjunction with an efficient microphone, because the sounds are completely modelled in terms of timbre. Namely, these speech sounds come from the mouth cavity, where there are completely formed in terms of timbre, and from where they then move via the auditory canal on the skull side into the auditory system. On the way to the external auditory canal, they are greatly weakened and substantially distorted; for this reason the reproduction of the speech sounds by means of resonator placed in the ear would provide unsatisfactory results, apart from the fact that we would be confronted here with an acoustic feedback which would make the duplex capability of the talk/listen headset impossible. Located directly in the area of the start of the outer bone 108 of the auditory canal (os tympanicum) on the skull side is the end of the zygqmatic arch 100 (arcus zygomaticus); the latter is adjoined in the downward direction by the articular process 102 of the ascending ramus of the jaw (processus condylaris mandibulae), the latter engaging into the lower limit of the zygomatic arch 100 (arcus zygomaticus) in an articulated manner. The reproduction of the speech sounds by means of preferably piezoelectric resonators, as are described under FIG. 3, which are placed in the area of the plane formed by the vertical 9, proves to be of high quality: resonators placed in the area of the zygomatic arch 100 produce a voice characterized by high tones; further below in the area of the articular process 102 of the ascending ramus of the jaw the original timbre will include a proportion of low tones. Indeed it is possible to determine that point along a plane to the vertical 9 which guarantees in the individual case the best possible reproduction of the most undistorted voice characteristic. With a view to a more comprehensible reproduction, it is readily possible here to achieve a specific correction by placing the microphones appropriately, because in terms of quality this indirect reproduction of a solid-borne sound not only depends on the quality of the microphone itself, but also on the given bone structure and on the timbre of the voice of the respective individual. The microphones 6, 7 are connected together with respect to voltage, as the line 8 is intended to indicate. The voltage picked up at the two microphones 6, 7 as well as the line 10 from the earphones 4a, (4b=FIG. 4) are combined to form a connecting cable 11 and led to the outside, and from there carried to a transmitting/receiving device on the person. It is of course possible for this device not to be wirebased, in accordance with the known prior art in this sector. The microphones 6, 7 connected to each other effect a neutralization of the tone amplitudes at the top and bottom in such a way that the reproduction of the voice, which is after all far removed from the natural place of speech emission, approximates in quality the original timbre, in conjunction with the abovementioned design of the microphone according to FIG. 3. In a normal case, positive results can be expected if the upper microphone 6 has at the zygomatic bone side a distance of 3-5 cm to the outer bone of the auditory canal (os tympanicus), while the lower microphone 7 is placed in the vertical 9 and has a distance of 3-10 cm with respect to the upper microphone 6. The current is supplied to the elements from a battery 16 located in an ear protection capsule 1 or 2, from which battery the supply of the individual elements is ensured. The power supply from the battery 16 is switched on and off automatically by a permanent magnet 17 with an explosion-proof reed switch (not visible in the figure) according to the following dynamics. If the headset is removed, then the tension is removed from the tensioned spring of the headband 3 which causes the battery 16 to be switched off by the reed switch placed at the capsule-side end of the head band 3; when the talk/listen headset is used again, on the other hand, the headband 3 is splayed, which then releases the current supply from the battery 16 again.

Figure 2:
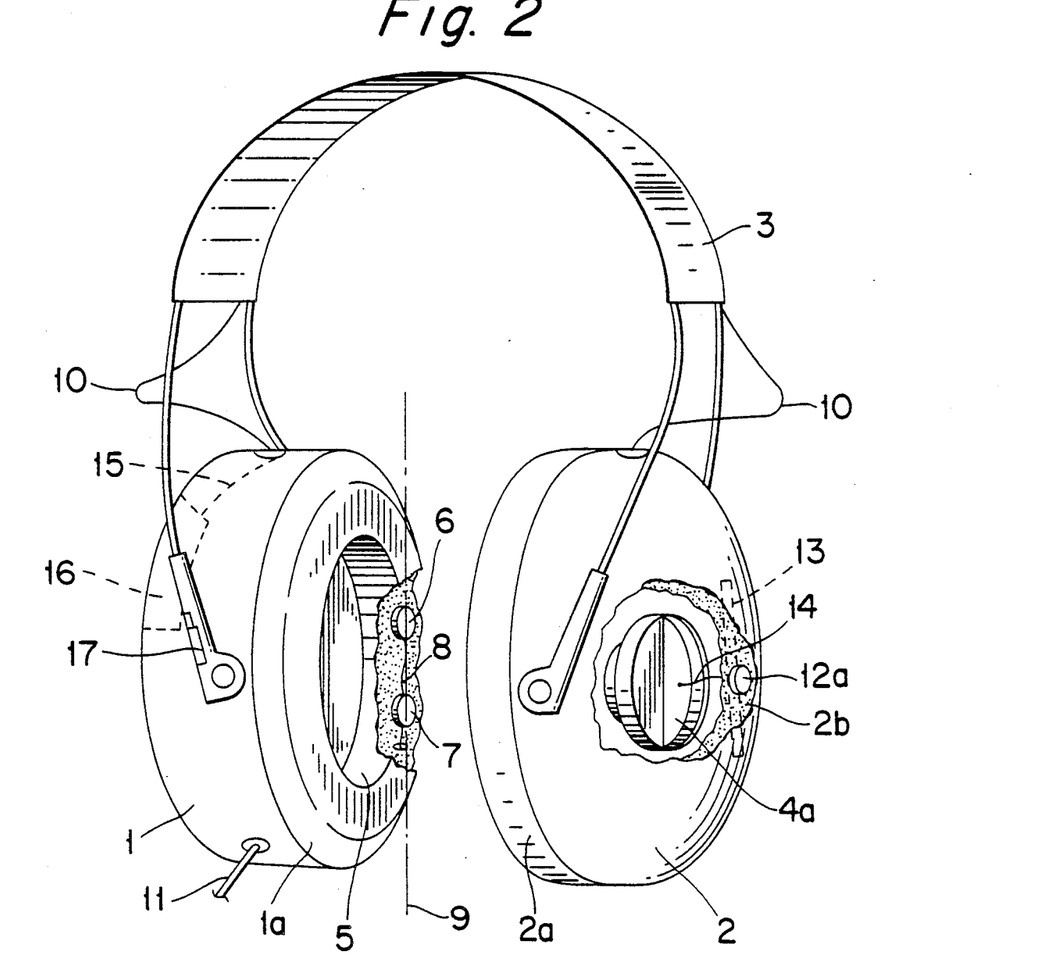
FIG. 2 shows a further talk/listen headset which, besides the functions of ear protection, receiving and sending, also permits background noises to be heard.

FIG. 2 shows an extension of the talk/listen headset which specifically cancels the noise cut off from the background noises without, however, having to forgo the advantages of ear protection. The ear protection capsules 1, 2 are each equipped with an outwardly directed receiving element 12a, (12b is not visible in capsule 1, but is evident from FIG. 4), which are directed towards the background noises. This talk/listen headset is furthermore extended to include an electronic component 13 which interacts with the microphones 6, 7, the earphones 4a, 4b (=FIG. 4) and the receiving elements 12a, 12b (=FIG.4), and the circuitry of which provides a communication priority in favour of the microphones and earphones and not in favour of the receiving elements: if there is a connection to a remote location, either via the microphones or the earphones, then this communication priority is always switched through; background noises are not forwarded from the receiving elements to the earphones because the communication priority has interrupted this circuit. During a communication phase, the ear protection capsules 1, 2 are dompletely cut off from background noises. After communication via the microphones and earphones has finished, the reception of the background noises via the receiving elements then start to function again, with a time delay set in the electronic component 13 or which can be set optionally, that is the wearer of the talk/listen headset has a relative access to the background noises despite ear protection cut off, in accordance with the volume level provided. In many setups such an extension provides inestimable assistance and necessity for the wearer, because the latter is not completely isolated with an important sensory organ from these surroundings during the communication pauses. Indeed, as practice has shown, an insulation represents a source of danger which should not be underestimated, in particular when carrying out difficult and dangerous work. It is also advantageous in other cases if one is not completely isolated, despite ear protection, from one's surroundings, that is contact is possible without having to remove the talk/listen headset each time. In order not to make the original protective function of the talk/listen headset ineffective, the electronic component 13 has means which regulate the background noises to preferably 30–85 decibels, regardless of the incoming volume level. According to experience, such means will serve to absorb the excess decibels without time delay so that the wearer of the talk/listen headset will always receive a filtered reception of the background noises. Even a bang in the immediate vicinity is heard in a weaker form. Thus, the widest variety of possible uses opens up here for the talk/listen headset described, above and beyond the first application according to FIG. 1: as an example of this, we will only cite the possibility here that this headset is excellently suitable for wearing in a firing range, especially if a direct communication with persons..in the immediate vicinity is required or desired between the individual firing, for instance during a training session in the presence of an instructor. The activation of the communication priority should preferable be carried out by means of voice sensing. This means that as soon as a radio-based or wire-based link to from the headset wearer is initiated, the receiving elements are instantly bypassed so that communication can take place via the microphones and the earphones without interference. A voice-controlled circuit of this type serves for automatically switching over the radio device to send/receive, consequently rendering unnecessary for this to be continually switched on and off manually. It is also important that the natural self control during speaking is not lost even during the use of the present talk/listen headset. In particular it is important during each switch-over to the communication priority that there is a self control over the wearer's own speech. For this purpose the electronic component 13 has a circuit which ensures a feedback between microphones and earphones when the communication priority is activated. This feedback furthermore makes possible a redundant control, which is justified in particular if the link to a remote location, either via radio or wire-based, is initiated by voice sensing, because here the uncertainties arising as regards whether one is "transmitting" or not are particularly predominant, at least more predominant than when the link is initiated by manual keying. It is of course possible to provide a key which permits the radio link, that is the communication priority, that is the voice sensing, to be switched off, whereupon the talk/listen headset wearer can .communicate with the immediate surroundings without interference over the microphones and/or earphones. The current supply to the various elements is also provided here by means of a battery 16, analogous to FIG. 1. As regards the circuit of the electronic component 13, refer to FIG. 4.

FIG. 3 shows a microphone reacting to solid-borne sound consisting of a piezoelectric resonator 6b, a mass-forming body 6a, an impedance converter 6f, a filter/equaliser 6g and a contact capsule 6c. The elements listed interact with one another, as the line 6d is capable of vibration if the resonator 6b lying thereunder is to be optimally impinged by the solid-borne sound. In this connection, the use of a contact capsule 6c having a residual capacity for swallowing the high frequency tones would have a negative effect. The resonator 6b is "sandwiched" between contact capsule 6c and a damping ring 6e. It is possible to affect the oscillation amplitudes from the resonator 6b to such an extent that a sharper resonance is achieved thereby, which leads to an improvement in the quality of reproduction, in that the piezoelectric resonator 6b physically interacts with the mass-forming body 6a, which is preferably made of a material with a high density which has a low absorbtion capacity with respect to oscillations, as is the case with a hard copper alloy, for example. In the mass-forming body 6a are also located the impedance converter 6f and the filter/equaliser 6g, which interact with the resonator 6b via the line 6d in terms of voltage, and contribute to further improving the qualitative degree of efficiency in the transmission of the voiced sounds towards greater speech comprehensibility: thus the impedance converter 6f performs an impedance matching to a downstream radio device, while the filter/equaliser 6g have an effect on the presence of speech.

Figure 4:
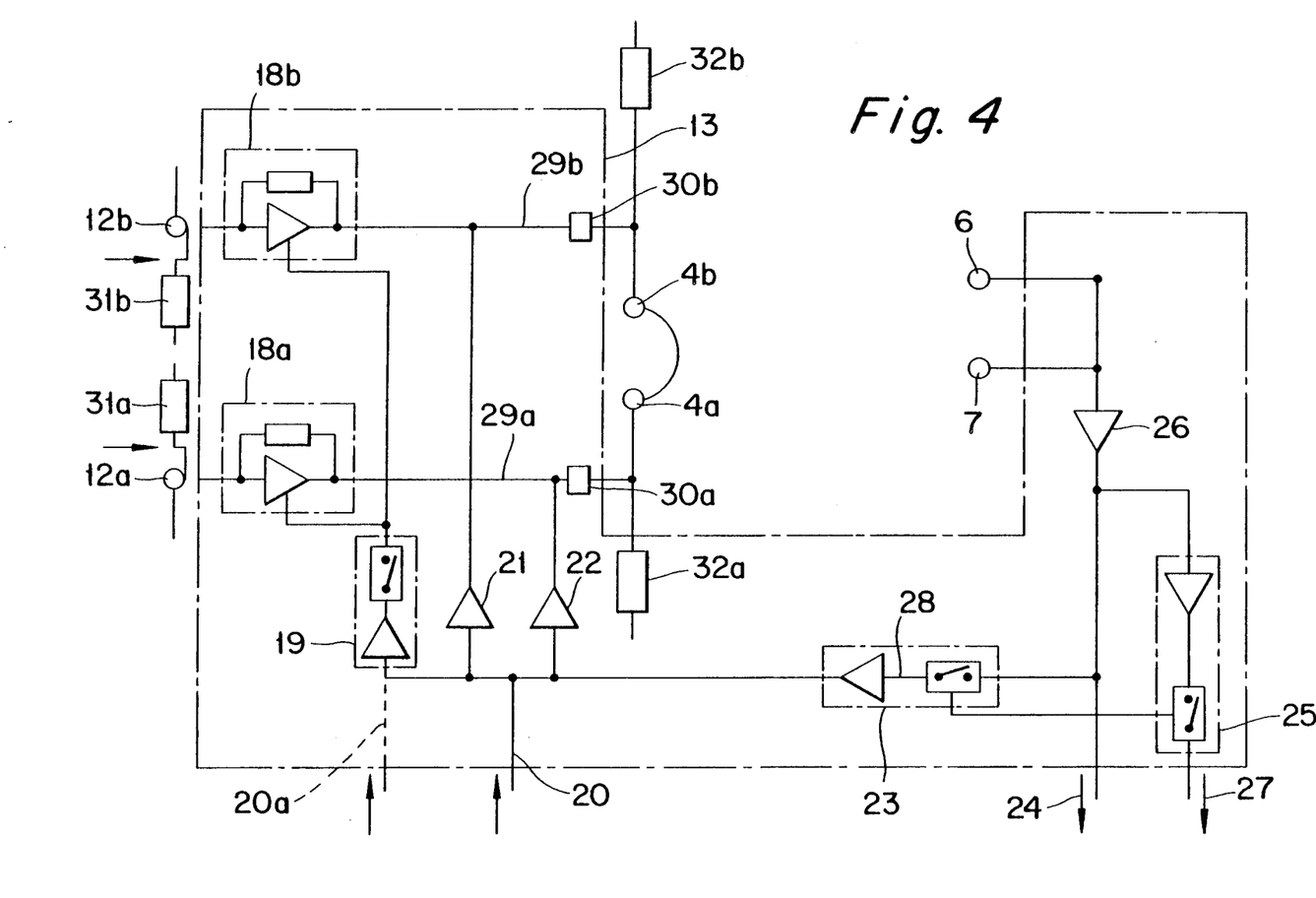
FIG. 4 shows a diagram of the circuitry of an electronic component integrated in the talk/listen headset for the extended function execution according to FIG. 2.

FIG. 4 shows the internal design as stipulated of the electronic component 13, already mentioned in part under FIG. 2. In this diagram the microphones 6, 7, the earphones 4a, 4b in each case located in an ear protection capsule 1, 2 and the receiving elements 12a, 12b, likewise accommodated in a ear protection capsule, can be seen. If the communication priority is activated, either by the wearer via the microphones 6, 7 or towards the wearer via the earphones 4a, 4b then a priority communication amplifier 19 switches over without delay, and the two receiving elements 12a, 12b are made ineffective with regard to sound level via the limiter compressor/expander 18a, 18b individually allocated and located in each hearing line 29a, 29b: background noises to the earphones 4a, 4b are thus interrupted, and the talk/listen headset again fully develops its function as ear protection. The signal coming in via a receiving channel 20 passes through the amplifiers 21, 22 and reaches the earphones 4a, 4b. Another circuit line, also on communication priority, starts from the microphones 6, 7: following an amplifier 26, the outgoing s is split in such a way that the one line forms an LF (i.e., low frequency) signal 24, and the other line forms a logic level signal 27 which is generated by a controller 25 and which can be used for transmitter control. On the one hand the logic level signal 27 is used externally for a transmitter keying, and on the other hand is used internally in the component for an LF control of a monitoring channel 28. In both cases, the activation of the communication priority, as is shown clearly in the diagram in FIG. 4, via the signal over receiving channel 20 and via the logic level signal 27, causes an interruption of the two receiving elements 12a, 12b, that is an interruption of the backgrounds noises to the earphones 4a, 4b. The abovementioned amplifiers 21, 22, which also convey the internal pulses from the microphones 6, 7 to the earphones 4a, 4b serve to maintain the voice control (monitoring) already described under FIG. 2. The priority communication amplifier 19 is set so that it switches over after 0.5-2 seconds, for example, when a signal does not arrive, be it via the receiving channel 20 or via a digital signal 20a arriving in parallel, as well as via the monitoring channel 28, and thus releases the receiving elements 12a, 12b again for receiving the background noises. The limiter/compressor/expanders 18a, 18b ensure that the volume level to the earphones 4a, 4b is regulated preferably to 30-85 decibels, regardless of the volume level of the incoming sound. The manual generation of the logic level signal 27 takes places conventionally, in that one of the two ear protection capsules 1, 2 has a switch (not shown on the various figures) which can be activated from the outside, and which also activates a controller 23 on the monitoring channel 28.

A redundant safety measure is provided in connection with the two limiter/compressor/expanders 18a, 18: as is known, as emerges from the above description, the latter filter or increase, respectively, the incoming sound to the two earphones 4a, 4b to a bandwidth between 30 and 85 decibels, depending upon the setting. This protective measure consists of two diodes 30a, 30b, which are located immediately following each limiter/compressor/expander 18a, 18b on the respective transmission hearing line 29a, 29b to the individual earphones 4a, 4b which perform the function, in the case of any failure or breakdown of the sound level conditioning of the incoming sound, of intervening in the limiter/compressor/expanders 18a, 18b in such a way that by means of these diodes 30a, 30b too high a sound level is always limited preferably to a maximum of 80 decibels in order to protect the hearing of the wearer redundantly. The circuit according to FIG. 4 is furthermore extended by two induction coils 31a, 31b which perform the function of induction receivers. If at least one ear protection capsule 1 or 2 contains an induction coil 31a, 31b, it is possible to communicate via a telephone without removing the talk/listen headset. For this purpose it is sufficient if the earpiece of the telephone receiver is placed against the corresponding ear protection capsule; the induction from the earpiece of the telephone receiver is captured by the induction coil 31a, 31b located in the ear protection capsule and forwarded to the earphones 4a, 4b. Since the present talk/listen headset can do without a lip microphone, the wearer can talk into the microphone piece of a telephone receiver without problems, as a result of which the present talk/listen headset is also extremely suitable for links via a field telephone. It is of course additionally advantageous if the inductive switching into the circuit of the electronic component 13 is provided for both ear protection capsules 1, 2, based on the daily observation that the ear used for telephoning is an individual feature.

If the present object is also intended for activities where the wearing of a protective helmet is absolutely necessary or is prescribed, as is the case for military pilots, for example, then the aforesaid elements of the ear protection capsules can be directly integrated in the protective helmet, or the top part of the outer shell of the ear protection capsule can be flattened to such an extent that it is possible to slip the protective helmet over it without problems.

Depending on the degree of miniaturization, the electronic component 13 can, of course, be a printed circuit of various size in the form of a board, which can easily be integrated in an ear protection capsule 1, 2 as is illustrated in FIG. 2 by the dashed outlines of the component 13.

Furthermore, in each case a vibrator 32a, 32b assigned to each earphone 4a, 4b can intervene in the circuit of the electronic component 13. When this is preferably to be provided emerges from the description of FIG. 5 below.

It is known from medical science that people already having hearing defects require a more intensive protection, for an already damaged hearing function is highly liable to suffer additional damage, already at medium volume levels, although the person itself does not perceive this, which obviously leads to no direct protective measures. In order to provide a remedy here, FIG. 5 indicates a possibility of how such an extension can be implemented for protecting people with defective hearing, while retaining the functional features of the talk/listen headset. At least one vibrator 32a, 32b located in each ear protection capsule 1, 2 is provided with an ear plug 33, which can be raised from the horizontal to the vertical manually and as required by a small wheel. Of course, other mechanisms are also conceivable for raising the ear plug 33 into the operational position, that is in the plane of the auditory canal. This ear plug 33 protects the person with a hearing defect from sound effects without preventing a communication from taking place as a result: the incoming sound causes the vibrators 32a, 32b to vibrate, the vibrations are then transferred to the respective ear plug 33, in order to be propagated in turn through the auditory canal to the stirrup/hammer/anvil. The sound thus no longer directly hits the hearing organs already sensitive as a result of hearing defects, but is converted into vibrations. An additional hearing aid on a vibration basis is likewise represented by an ear reed 35 likewise connected to the vibrators 32a, 32b which can likewise be swung open, as required, and placed at the level of the hearing bone behind the ear. The person with defective hearing is thus protected optimally from sound influences, without thereby being unable to communicate. If neither the plug 33 nor the ear reed is necessary, the two elements remain retracted, in such a way that they cannot become a nuisance to the talk/listen headset wearer. In the case of a talk/listen headset for persons with hearing defects, it is furthermore advantageous if the limiter/compressor/expander 18a, 18b is extended with an additional equaliser (not shown) in order to be able to set therewith in each case the optimum hearing curve depending on the degree of hearing damage of the respective person.

Figures 5, 6:
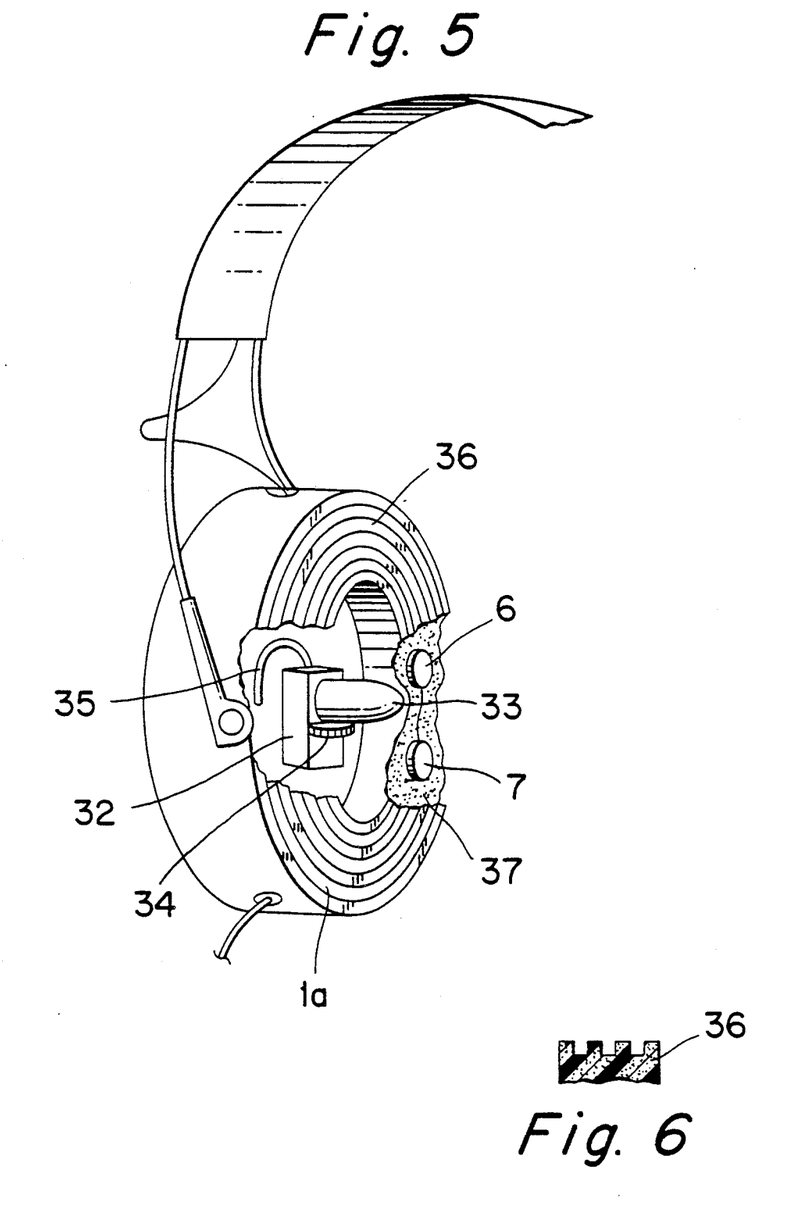
FIG. 5 shows a further design of the talk/listen headset which contains aids for people with hearing defects.
FIG. 6 shows a section through the surface of an ear protection capsule on the ear side

Provision for spectacle wearers is provided in that the cushions 1a, 1b of each ear protection capsule 1, 2 are provided with concentric grooves 36, as emerges from FIG. 6, so that the spectacle legs can be enclosed by the grooved surface in a sealing manner. An additional protection for the microphones 6, 7 from external interference is achieved, as already mentioned above, by the niches 37 visible here, in that the microphones 6, 7 are individually located therein.

Figure 8:
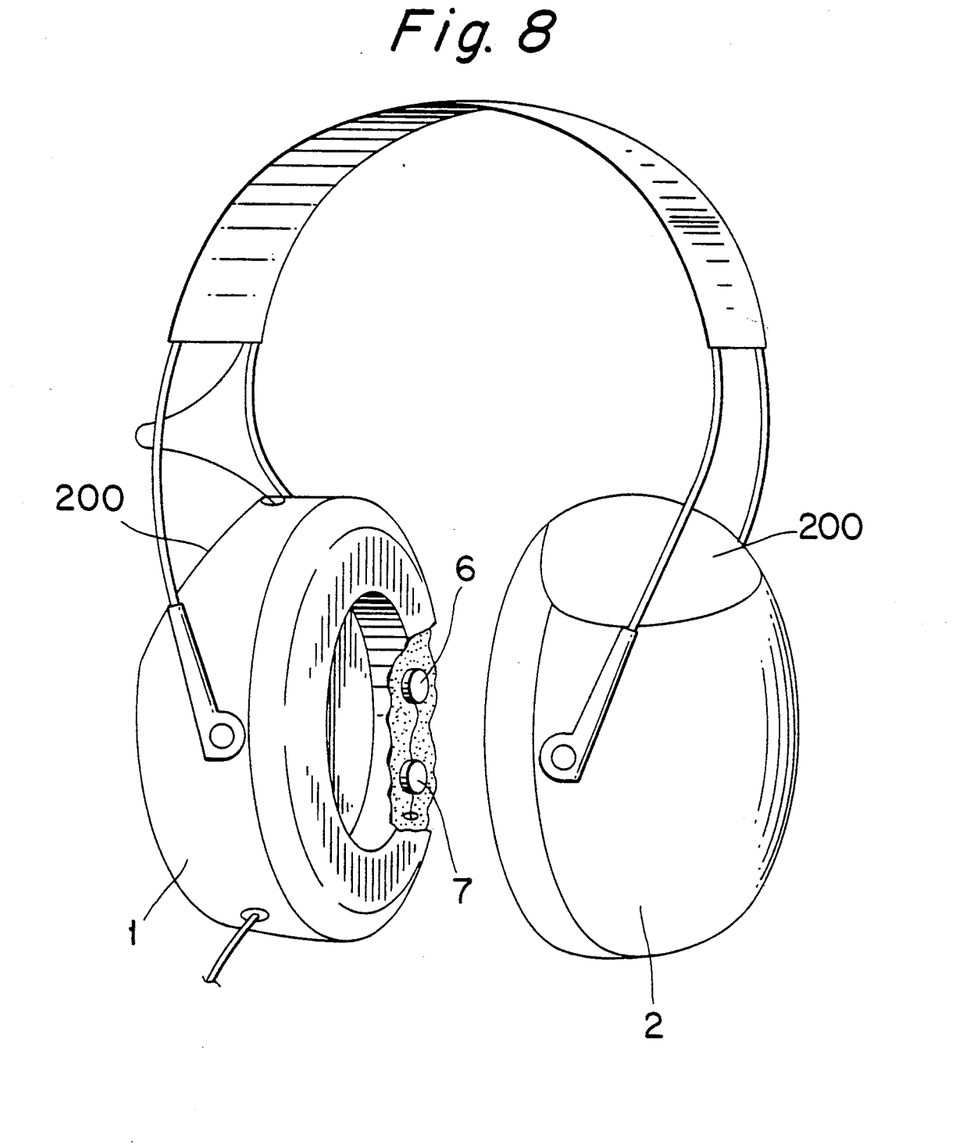
FIG. 8 is a perspective view of a third embodiment of the talk/listen headset of the present invention.

As shown in FIG. 8, a third embodiment of the talk/listen headset may include flattened areas 200 on top parts of the outer shells of the ear protection capsules 1, 2.

We claim:

1. A talk/listen headset, comprising:
   a pair of ear protection capsules;
   a first microphone;
   mounting means for mounting said first microphone in one of said ear protection capsules such that said first microphone is positioned, when said headset is worn by a person, in an area of an end of the zygomatic arch of the person;
   a second microphone;
   mounting means for mounting said second microphone in one of said ear protection capsules such that said second microphone is positioned, when said headset is worn by a person, in an area of the articular process of the ascending ramus of the person's jaw; and
   an earphone integrated into at least one of said ear protection capsules.

2. A talk/listen headset according to claim 1, wherein voltage outputs of said first and second microphones are connected.

3. A talk/listen headset according to claim 1, wherein said first microphone is positioned a distance of 3-5 cm from the outer bone of the person's auditory canal, and said second microphone lies in a vertical plane with said first microphone a distance of about 3-10 cm from said first microphone.

4. A talk/listen headset, comprising:
   at least one earphone;
   an outwardly-directed receiving element for receiving a background noise;
   an electronic component which includes
      means for regulating a sound level of the background noise received by said receiving element to a middle sound level, and for transmitting the background noise at said regulated sound level to said earphone,
      a plurality of channels, and
      means for setting a communications priority such that reception and transmission of the background noise remains interrupted when one of said channels is activated;
   at least one microphone for picking up solidborne sound; and
   a pair of ear protection capsules said earphone and said microphone being integrated into said ear protection capsules.

5. A talk/listen headset according to claim 4, wherein a priority communication amplifier can be activated via a first receiving channel or a second digital receiving channel to said earphone, wherein a monitoring channel to said earphone via said priority communication amplifier can be activated via a first LF (low frequency) channel from said microphone via an LF controller, wherein a transmitter key can be activated externally of said electronic component and said monitoring channel internal to the component can be activated via said LF controller by means of a second logic level channel from said microphone, and wherein redundant means for redundantly limiting a sound level of the background noise received by said receiving element is connected downstream of said regulating means.

6. A talk/listen headset according to claim 4, wherein at least one induction coil interacts with said electronic component.

7. A talk/listen headset according to claim 4, wherein at least one vibrator, one positionable ear plug and a positionable ear reed are integrated into said ear protection capsules, and wherein said regulating means includes an equaliser.

8. A talk/listen headset according to claim 4, wherein said regulatory means includes a limiter/compressor/expander.

* * * * *